US012589192B2

(12) United States Patent
Wallace et al.

(10) Patent No.: US 12,589,192 B2
(45) Date of Patent: Mar. 31, 2026

(54) PORTABLE DIALYSIS SYSTEM

(71) Applicant: Quanta Dialysis Technologies Limited, Alcester (GB)

(72) Inventors: Mark Wallace, Alcester (GB); Clive Buckberry, Alcester (GB); Brett Walker, Alcester (GB); Nicholas Copeland, Alcester (GB); Bradley Pavitt, Mildenhall (GB)

(73) Assignee: QUANTA DIALYSIS TECHNOLOGIES LIMITED, Warwick (GB)

( * ) Notice: Subject to any disclaimer, the term of this patent is extended or adjusted under 35 U.S.C. 154(b) by 515 days.

(21) Appl. No.: 17/922,776

(22) PCT Filed: Apr. 9, 2021

(86) PCT No.: PCT/EP2021/059304
§ 371 (c)(1),
(2) Date: Nov. 1, 2022

(87) PCT Pub. No.: WO2021/219346
PCT Pub. Date: Nov. 4, 2021

(65) Prior Publication Data
US 2023/0166016 A1 Jun. 1, 2023

(30) Foreign Application Priority Data
May 1, 2020 (GB) ...................................... 2006488

(51) Int. Cl.
B01D 36/02 (2006.01)
A61M 1/14 (2006.01)
(Continued)

(52) U.S. Cl.
CPC ........ A61M 1/1672 (2014.02); A61M 1/1563 (2022.05); A61M 1/1654 (2013.01);
(Continued)

(58) Field of Classification Search
CPC .............. A61M 1/1563; A61M 1/1672; A61M 1/1654; A61M 1/1656; A61M 1/1674;
(Continued)

(56) References Cited

U.S. PATENT DOCUMENTS

2010/0018923 A1 1/2010 Rohde et al.
2010/0051552 A1* 3/2010 Rohde ..................... A61M 1/28
210/644
(Continued)

FOREIGN PATENT DOCUMENTS

WO 96/25214 A1 8/1996

OTHER PUBLICATIONS

European Patent Office, "International Search Report and Written Opinion," issued in related International Patent Application No. PCT/EP2021/059304, mailed Jun. 14, 2021 (8 pages).
(Continued)

*Primary Examiner* — John Kim
(74) *Attorney, Agent, or Firm* — The Marbury Law Group, PLLC

(57) ABSTRACT
A dialysis system (10) comprising a dialysis machine (20) and a water purification system (30). The water purification system (30) comprising a pre-treatment system (10) and a primary treatment system (80). The water purification system (30) is provided within a portable unit (90) defining an enclosure. The dialysis machine (20) is removably provided on an upper surface of the enclosure of the portable unit (90).

12 Claims, 8 Drawing Sheets

(51) Int. Cl.

| | |
|---|---|
| *A61M 1/16* | (2006.01) |
| *A61M 1/28* | (2006.01) |
| *B01D 61/02* | (2006.01) |
| *C02F 1/44* | (2023.01) |
| *C02F 9/00* | (2023.01) |
| *A61M 1/36* | (2006.01) |

(52) U.S. Cl.

CPC ........ *A61M 1/1656* (2013.01); *A61M 1/1674* (2014.02); *A61M 1/287* (2013.01); *B01D 36/02* (2013.01); *B01D 61/02* (2013.01); *B01D 61/025* (2013.01); *C02F 1/441* (2013.01); *C02F 9/00* (2013.01); *A61M 1/3643* (2013.01); *A61M 2205/053* (2013.01); *A61M 2207/00* (2013.01); *A61M 2209/08* (2013.01)

(58) Field of Classification Search

CPC ................ A61M 1/287; A61M 1/3643; A61M 2205/053; A61M 2207/00; A61M 2209/08; B01D 36/02; B01D 61/02; B01D 61/025; C02F 1/441; C02F 9/00

See application file for complete search history.

(56) References Cited

U.S. PATENT DOCUMENTS

| | | | |
|---|---|---|---|
| 2011/0189048 A1 | 8/2011 | Curtis et al. |
| 2015/0083647 A1 | 3/2015 | Meyer et al. |
| 2015/0314055 A1 | 11/2015 | Hogard et al. |

OTHER PUBLICATIONS

European Patent Office, "International Preliminary Report on Patentability," issued in related International Patent Application No. PCT/EP2021/059304, mailed Oct. 27, 2022 (6 pages).

Intellectual Property Office, "Search Report," issued in related United Kingdom Patent Application No. GB2006488.7, dated Oct. 28, 2020 (1 page).

\* cited by examiner

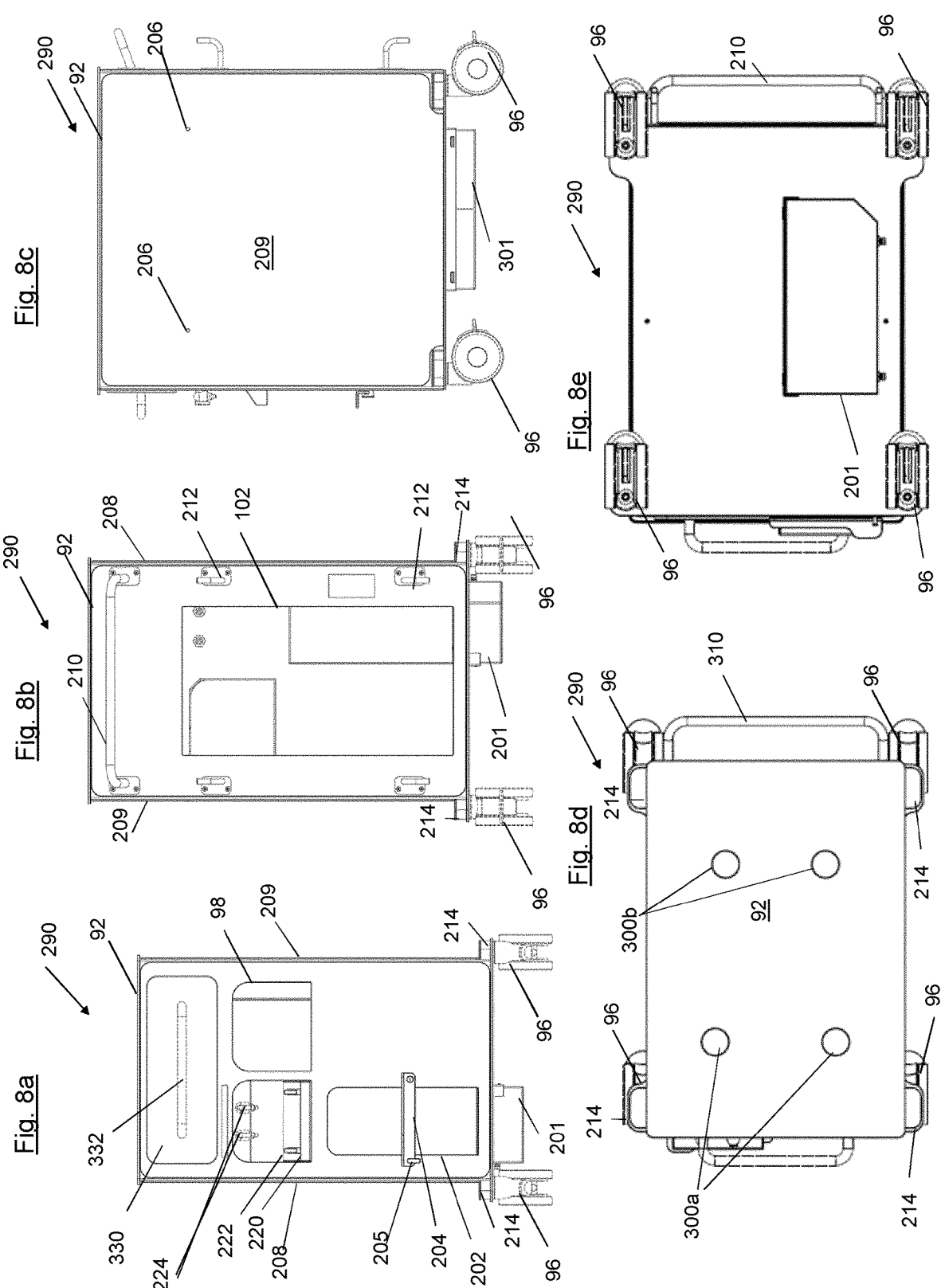

PORTABLE DIALYSIS SYSTEM

CROSS-REFERENCE TO RELATED APPLICATIONS

This application claims priority to International Patent Application No. PCT/EP2021/059304, filed Apr. 9, 2021, and entitled "Portable Dialysis System," which in turn claims benefit of and priority to GB2006488.7, filed May 1, 2020, and entitled "Portable Dialysis System." The disclosures of each of the above-referenced applications are herein incorporated by reference in their entireties.

FIELD OF THE INVENTION

The present invention relates to operation of a portable dialysis system, and in particular to a portable dialysis system comprising a dialysis machine and a water purification system.

BACKGROUND TO THE INVENTION

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis.

In peritoneal dialysis treatment, a dialysate fluid is run through a tube into the peritoneal cavity. The fluid is left in the cavity for a period of time in order to absorb the waste products, and is subsequently removed through the tube for disposal.

It is common for patients in the early stages of treatment for a longstanding renal condition to be treated by peritoneal dialysis before progressing to hemodialysis at a later stage.

In hemodialysis, the patient's blood is removed from the body by an arterial line and treated by a dialysis machine before being returned to the patient's body by a venous line. The machine passes the blood through a dialyser containing tubes formed from a semi-permeable membrane. On the exterior of the semi-permeable membrane is a dialysis fluid. The semi-permeable membrane filters the waste products and excess fluid from the blood into the dialysis fluid. The membrane allows the waste and a controlled volume of fluid to permeate into the dialysis fluid whilst preventing the loss of larger more desirable molecules, like blood cells and certain proteins and polypeptides.

The action of dialysis across the membrane is achieved primarily by diffusion (the migration of molecules by random motion from a region of higher concentration to a region of lower concentration).

Fluid removal (otherwise known as ultrafiltration) is achieved by altering the hydrostatic pressure of the dialysis fluid side of the membrane, causing free water to move across the membrane along the pressure gradient.

The correction of uremic acidosis of the blood is achieved by use of a bicarbonate buffer. The bicarbonate buffer also allows the correction of the blood bicarbonate level.

The dialysate fluid consists of a sterilized solution of mineral ions. These ions are contained within an acid buffer which is mixed with the purified water and bicarbonate base prior to delivery to the dialyser.

Production of dialysis fluid is described in the applicant's own applications WO2016/120415, WO2010/146342, WO2010146344 and WO2014/155121 the entire contents of each are expressly incorporated herein by reference.

In simple terms, dialysis water is mixed with the bicarbonate buffer and the acid buffer to create a dialysis fluid. Dialysis water is defined by the standard ISO 23500-3:2019. Dialysis fluid is defined by the standard ISO 23500-5:2019.

The composition of the dialysis fluid needs to be tightly controlled to keep the patient's blood at an optimal composition. Typically, the dialysis fluid is passed through the dialyser once before being discarded to ensure that the composition of the dialysate solution remains constant. A single dialysis session takes four hours with approximately 120 liters of dialysis fluid being used per session. Thus a single dialysis session requires a significant volume of dialysis water.

Patients being treated for a renal condition are typically required to either attend a medical facility, either in an acute setting, for example an intensive care ward or in a chronic setting, for example a dialysis ward or dialysis center. Some patient's requiring treatment for chronic conditions may be able to conduct dialysis at home.

Given the varied treatment settings, there is also a variation in the availability of dialysis water.

For example a hospital dialysis ward may have access to a hospital water ring main, where dialysis water is provided from a hospital plant room. This may differ from an acute setting, such as an intensive care unit, where there is no provision of a hospital ring main.

This may also differ from home use, where the only plentiful source of water is through the domestic tap. Existing home dialysis water generation installations may therefore comprise a permanent fixed installation of pipework and filters, bolted to a patient's wall. Each such installation is bespoke to each home, with no consideration of usability. Furthermore such installations are unsightly and do not contribute to the well-being of the patient. Yet furthermore, such installations are time consuming to install and remove.

Further, given the varied treatment settings for dialysis, there is also a need to be able to move the dialysis machine and/or dialysis water generation installation, for example between hospital wards or to a patient's home.

There is therefore a need for an improved portable dialysis system.

SUMMARY OF THE INVENTION

According to a first aspect of the present invention there is provided a dialysis system comprising: a dialysis machine; and a water purification system, the water purification system comprising a pre-treatment system; and a primary treatment system, wherein the water purification system is provided within a portable unit defining an enclosure, and wherein the dialysis machine is removably provided on an upper surface of the enclosure of the portable unit.

The dialysis system provides a portable unit such that both the dialysis machine and water purification system may be moved to the location of need. Further, since the dialysis machine is removably provided on an upper surface of the enclosure of the portable unit, there is an increased flexiblity in the usage of both the dialysis machine and the water purification system. The portable unit provides a compact solution suitable for home and hospital use. Advantageously the portable unit may be easily moved around, for example within an intensive care unit where space is at a premium.

The pre-treatment system may be arranged on a removable panel of said enclosure. The removable panel may be an internal panel. Such an arrangement means that the water purification system comprising the pre-treatment system and the primary treatment system may be removed from the portable unit, leaving the dialysis machine and portable unit only. This is advantageous in situations where the treatment setting already includes the necessary equipment for producing dialysis water and thus means that the removed water purification system may be used elsewhere. The space remaining can be used for storage, for example, drawers may be placed in the space. The drawers may be used to contain consumables such as fluid lines, lumen spikes, catheters, needles, etc. Alternatively, a cupboard may be placed in the space.

The RO machine may be removed, serviced and temporarily replaced by an alternative RO machine. As such, the trolley space is not constrained to a single make or design of RO machine. Multiple different RO makes and designs may be retained within the space.

The pre-treatment system may be arranged along a side panel of said enclosure.

The pre-treatment system may comprise a fluid path including a particulate filter, a primary carbon filter and a secondary carbon filter.

The pre-treatment system may be removed, serviced and temporarily replaced by an alternative pre-treatment system. As such, the trolley space defined by the enclosure for the pre-treatment system is not constrained to a single make or design of pre-treatment system. Multiple different pre-treatment system makes and designs may be retained within the space. Further, individual components of the pre-treatment system may be removed, serviced and temporarily replaced by alternative individual components.

The pre-treatment system may further comprise a port for connecting water softener. Providing a water softener port allows a water softener to be introduced to the pre-treatment system in areas with hard water necessitating water softening. Where water softening is not required, no water softener need be attached. The pre-treatment system may therefore be used in a number of different locations with different water qualities.

The primary treatment system may comprise a reverse osmosis machine. The reverse osmosis machine may have a control panel. A window may be formed in the enclosure aligned with the control panel of the reverse osmosis machine.

Alternatively, the primary treatment system may comprise a deionisation system. The deionisation system may have a control panel. A window may be formed in the enclosure aligned with the control panel of the deionisation system.

Additionally, the primary treatment system may further comprise an endotoxin retentive filter and/or an ultraviolet light system.

The portable unit may be a trolley. The trolley may have four castors. The four castors may be arranged at four corners of the enclosure. At least one of the castors may include a lockable brake. Preferably all four castors each include a lockable brake.

The portable unit may have a work-surface. The work-surface is deployable. The work-surface may be a shelf or a drawer. Having a deployable work-surface allows for the user of the portable unit to prepare consumables and fluid lines required for a dialysis treatment easily.

The portable unit may have a number of dialysis machine mounts. The dialysis machine mounts are sized to retain a portion of the dialysis machine. Preferably the number of dialysis machine mounts is four. Preferably the dialysis machine mounts are sized to retain a foot or feet of the dialysis machine.

The dialysis machine mounts have a defined orientation, such that the dialysis machine when mounted on the portable unit is always mounted in the same direction. Preferably this direction is a forward direction.

The enclosure may be formed from flat sheet plastic. Forming the enclosure from flat sheet plastic allows for tooling free fabrication, expedited manufacture and time to market, and low development costs. Windows, doors and access panels may be included.

The access panels may be removably mounted on the portable unit. Preferably the access panels may be retained using a latch or pin.

The enclosure may further comprise a sump suitable for collecting leaking fluid from the water purification system. Preferably wherein the sump is removable for ease of cleaning, and/or removal of filters. The sump may have a leak sensor suitable for detecting a leak.

The enclosure may have an acid canister window suitable for accessing an acid canister in an acid canister space. The acid canister window may have a pivoting bar suitable for retaining an acid canister within the acid canister space.

The portable unit may be between approximately 800 and 970 mm in height. This means that the dialysis machine is at the optimum height for operational purposes.

According to a second aspect of the present invention there is provided a method of forming a dialysis system comprising the steps of: providing a dialysis machine; and a water purification system, the water purification system comprising a pre-treatment system; and a primary treatment system, forming a portable unit defining an enclosure, housing the water purification system within the portable unit, and providing the dialysis machine on an upper surface of the enclosure of the portable unit.

The pre-treatment system is provided along a removable panel of said enclosure.

BRIEF DESCRIPTION OF THE DRAWINGS

Embodiments of the present invention will now be described, by non-limiting example only, with reference to the accompanying drawings, in which:

FIGS. 8a to 8e show front, rear, side, upper and lower views of the portable unit of FIG. 7.

DESCRIPTION OF EMBODIMENTS OF THE INVENTION

The following detailed description and figures provide examples of how the present invention can be implemented and should not be seen as limiting examples, rather illustrations of how the various features of the convective operation device disclosed herein can be used. Other optional variations will be evident upon a reading of the following description in light of the figures.

Figure 1:
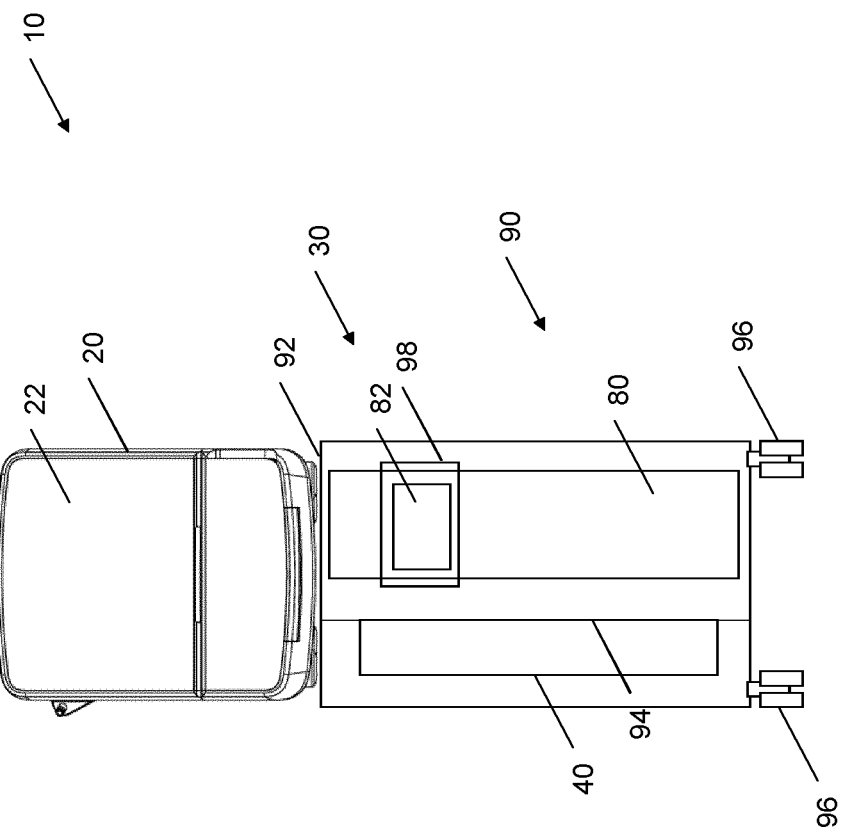
FIG. 1 shows a schematic of a dialysis system comprising a dialysis machine, a water purification system and a portable unit.

Referring to FIG. 1, a dialysis system, generally referred to as 10, is shown. The dialysis system 10 comprises a dialysis machine 20, a water purification system 30 and a portable unit 90.

The dialysis machine 20 is responsible for the production of dialysis fluid, and the controlled pumping of the dialysis fluid to and from a dialyser, as well as the controlled pumping of a patient's blood to and from the dialyser as is known in the art. The dialysis machine 20 has a dialysis machine control panel 22. The control panel 22 is a touch screen interface.

The water purification system 30 comprises a pre-treatment system 40 and a primary treatment system 80.

Figure 2:
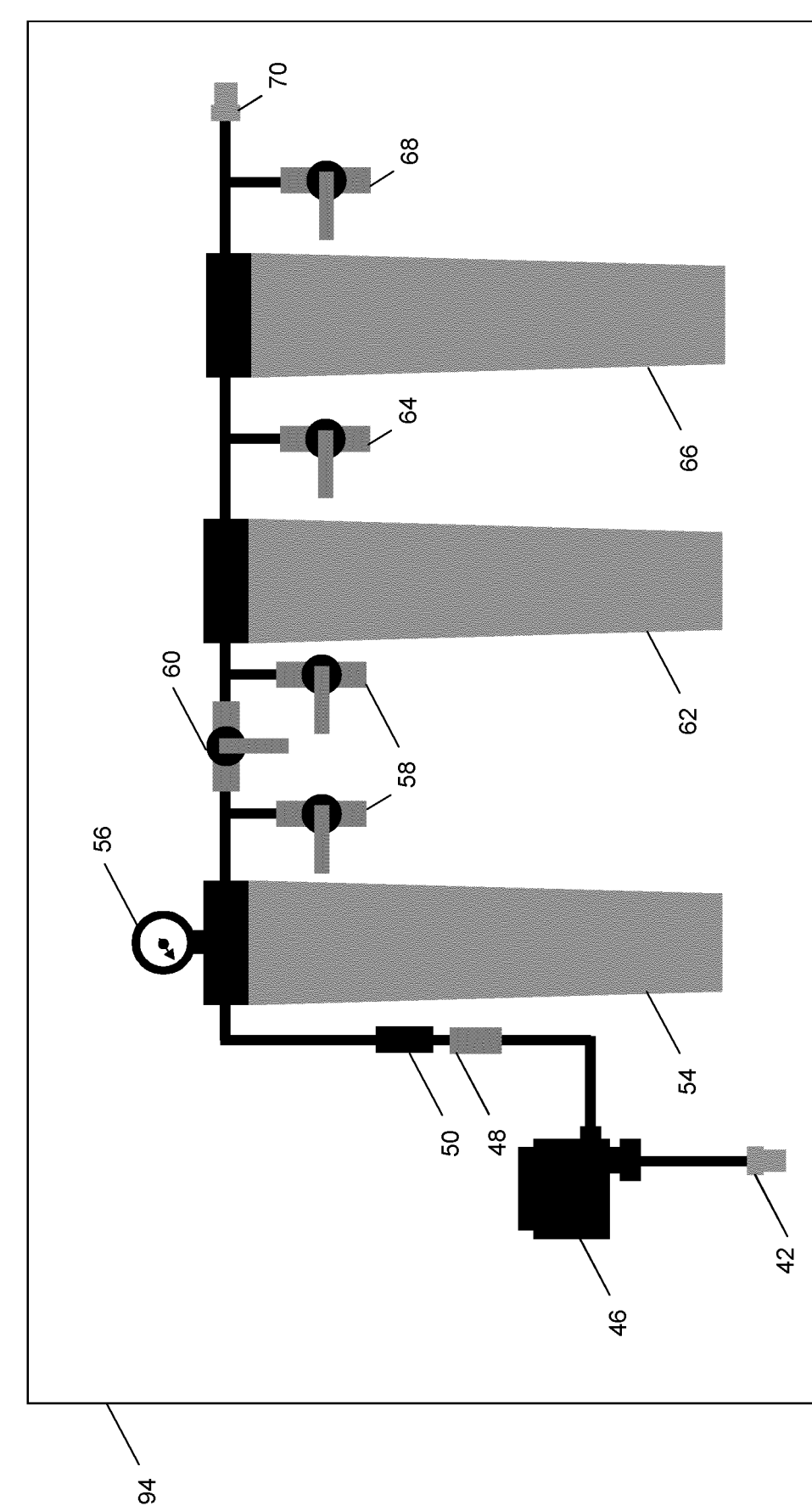
FIG. 2 shows a detailed schematic view of a pre-treatment system of the water purification system of FIG. 1.
Figure 3:
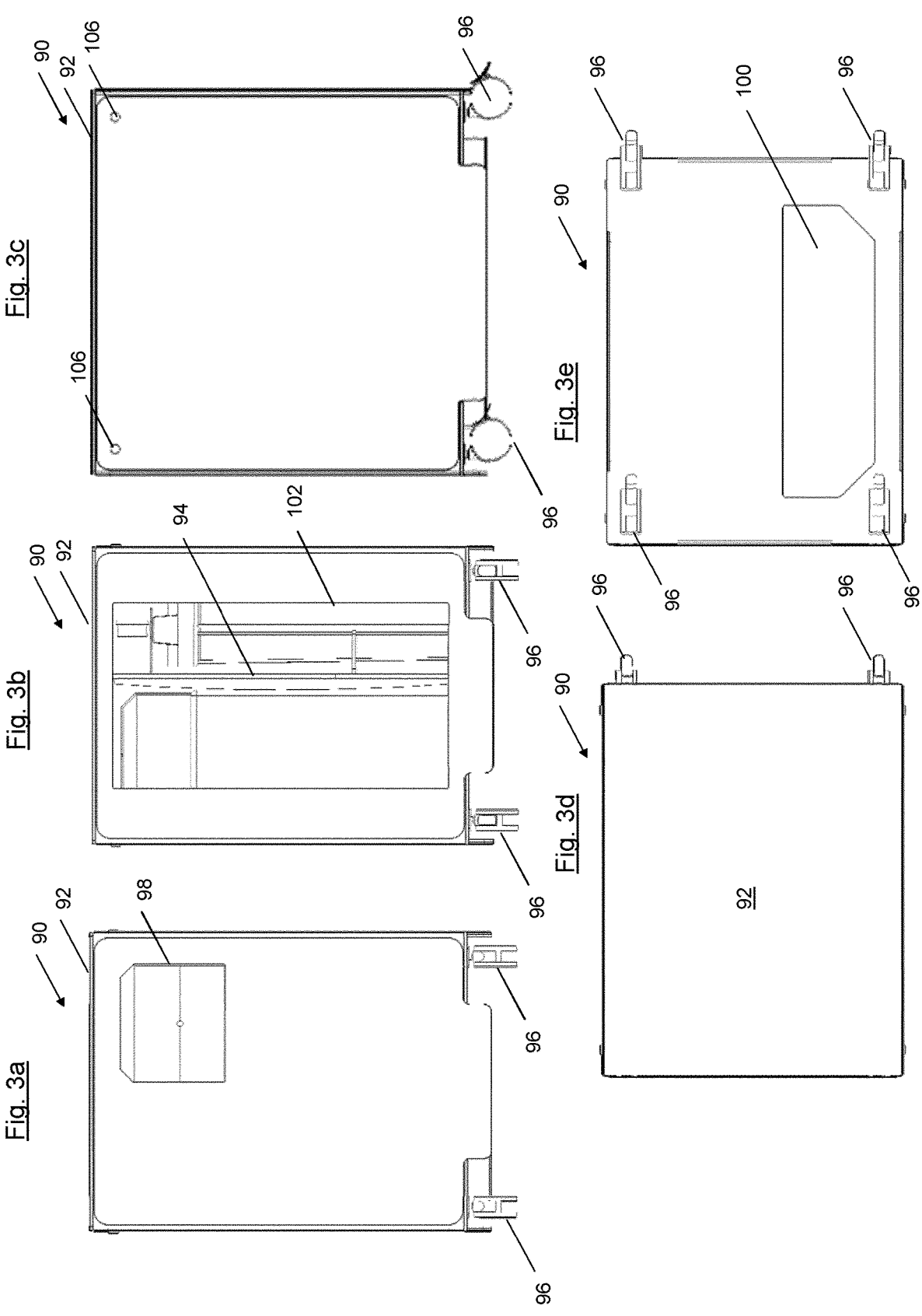
FIGS. 3a to 3e show front, rear, side, upper and lower views of the portable unit of FIG. 1.
Figure 4:
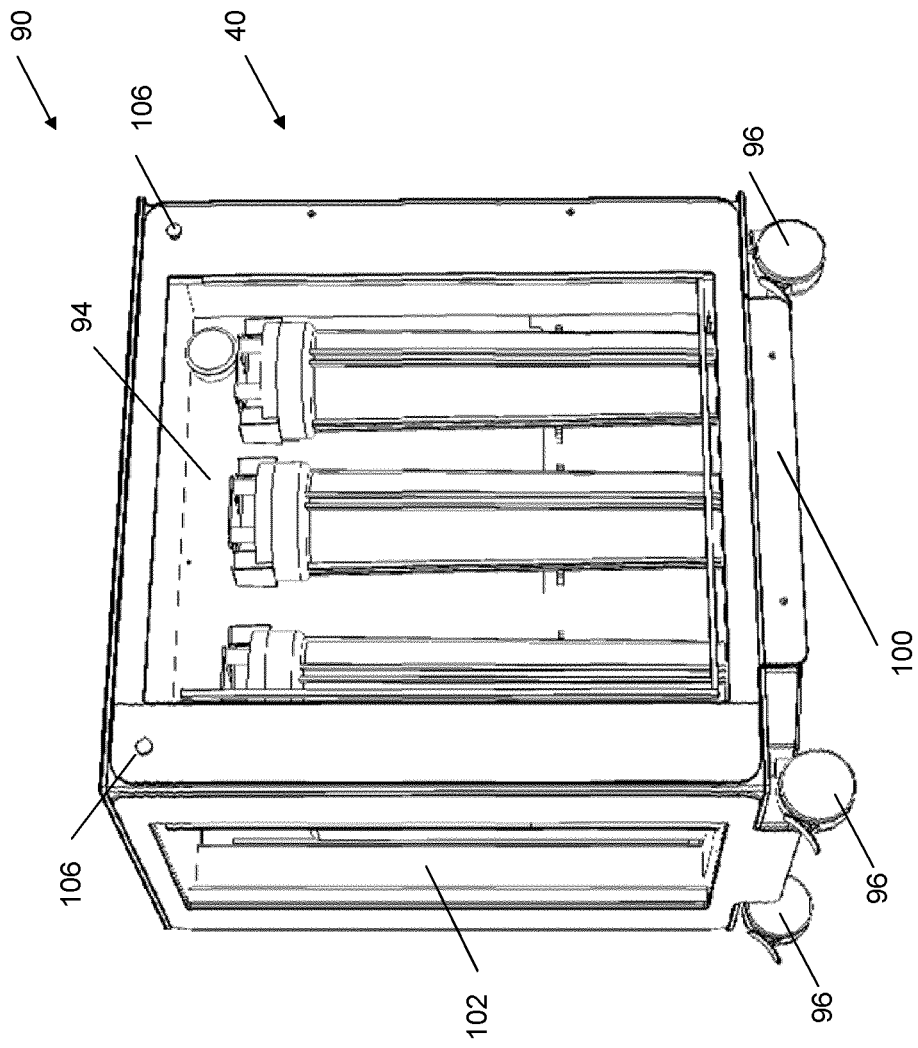
FIG. 4 shows a partial cut-away perspective view of the portable unit of FIG. 1.

The pre-treatment system 40 is shown in detail in FIG. 2. The pre-treatment system 40 comprises a fluid path having an inlet fitting 42 fluidly connected to a leak detector 46. The leak detector 46 comprises a valve and a leak sensor 44 as will be described in more detail below. A back flow prevention device 48 is fluidly connected downstream of the leak detector 46. A pressure reducing valve 50 is fluidly connected downstream of the back flow prevention device 48.

The pre-treatment system 40 further comprises three 20 inch height filter housings. The filter housings are a particulate filter, in this case a 5 µm depth filter 54, a primary carbon filter 62 and a secondary carbon filter 66. The primary carbon filter 62 is fluidly connected downstream of the 5 µm depth filter 54. The secondary carbon filter 66 is fluidly connected downstream of the primary carbon filter 62.

The 5 µm depth filter 54 filter housing is provided with a differential pressure gauge 56.

Fluidly connected between the 5 µm depth filter 54 and the primary carbon filter 62, an external softener bypass 58 is provided. The softener bypass 58 may be connected to a water softener should local water requirements require water softening. At this portion of the fluid path, an external softener can be added if required. Alternatively, if no external softener is required, a bypass isolator tap 60 allows fluid flow directly between the 5 µm depth filter 54 and the primary carbon filter 62.

A chlorine sample port 64 is provided downstream of the primary carbon filter 62.

A second tap 68 is provided downstream of the secondary carbon filter 66. The second tap 68 is used for priming the filters 54, 62, 66.

The fluid path of the pre-treatment system 40 terminates in an outlet fitting 70.

The primary treatment system 80 is a reverse osmosis machine. The primary treatment system 80 has a primary treatment system control panel 82.

In an alternate embodiment the primary treatment system 80 is a deionisation system. The deionisation system may include a control panel. Additionally, the primary treatment system may further comprise an endotoxin retentive filter and/or an ultraviolet light system.

The water purification system 30 is provided within the portable unit 90.

The portable unit 90 defines an enclosure. The enclosure comprises a cuboid having a left side panel, a right side panel, a front panel, a rear panel, an upper panel and a lower panel. The upper panel has an upper surface 92. The panels are mounted to a metal frame. The frame provides rigidity and strength to the portable unit 90.

An internal panel 94 extends between the front panel and the rear panel, parallel to the left side panel and the right side panel. The internal panel 94 divides the enclosure into two separate chambers, a left chamber and a right chamber. The internal panel 94 may be fastened to the frame or the front panel and the rear panel. Alternatively, the internal panel 94 may be slotted into groves provided in the frame or in the front panel and the rear panel.

The pre-treatment system 40 is arranged in the left chamber. The pre-treatment system 40 is fastened to the internal panel 94. Alternatively, the pre-treatment system may be arranged along an inwardly facing surface of the left side panel of the enclosure. The left side panel may be attached to the enclosure via a hinge.

The primary treatment system 80 is arranged in the right chamber. The enclosure has a window 98. The window 98 is provided in the front panel. The window 98 is aligned with the primary treatment system control panel 82 when the primary treatment system 80 is positioned on the lower panel within the enclosure.

A rear access window 102 is provided in the rear panel. The rear access window 102 provides access to both the pre-treatment system 40 arranged in the left chamber and the primary treatment system 80 arranged in the right chamber.

A sump 102 is provided in the lower panel, in the left chamber and aligned with the pre-treatment system 40. The leak sensor 44 of the leak detector 46 is placed in the sump at its lowest point. The lower panel include sloped channels which lead to the sump 102. The sloped channels extend across the width of the lower panel and thus can collect any leakage from either of the pre-treatment system 40 and the primary treatment system 80. In usage, when the leak sensor 44 detects the presence of water in the sump, the valve of the leak detector 46 is activated to shut off the water supply and prevent further leakage.

The enclosure is formed from flat sheet plastic which is mounted to the metal frame.

The internal panel 94 is removable.

The left side panel, the right side panel, the front panel, the rear panel, and the upper panel are removable.

The sheet plastic may be cleaned according to medical standards. The metal frame is encased in plastic such that there is no exposed metal even when panels are removed.

Each of the left side panel, the right side panel, the front panel, the rear panel, are arranged in slots provided in the plastic encasing the metal frame, and fastened to the plastic encasing the metal frame at the upper ends by two fasteners 106.

The portable unit 90 is a trolley. The trolley has four castors 96. Each castor 96 is provided at a corner of a lower surface of the lower panel of the enclosure. Each of the castors 96 have a lockable brake.

The portable unit 90 may be provided with handles. The portable unit 90 may be provided with hooks. The hooks may be suitable for hanging saline or other consumables for dialysis treatment. The portable unit 90 may include one or more pull out shelves. A lower pull out shelf may be suitable for housing an acid canister when using the dialysis machine 20. An upper pull out shelf may be suitable for extending the working area level with the upper surface 92.

The dialysis machine 20 is removably provided on the upper surface 92 of the enclosure of the portable unit 90. The dialysis machine 20 can be oriented according to need. For example the dialysis machine 20 may be forward facing as shown in FIG. 1, or the dialysis machine 20 may be oriented to face a side. This supports both clinician led dialysis and patient led dialysis.

The enclosure is approximately 0.7 m high by 0.6 m wide and 0.7 m deep. Together with the castors 96 the portable unit stands at approximately 0.75 mm high, such that the upper surface 92 of the enclosure of the portable unit 90 is 0.75 m above the floor, in use.

Usage

The dialysis system 10 comprising the dialysis machine 20 and the water purification system 30 allows for complete dialysis fluid preparation from a tap water source.

Tap water is generally understood to be equivalent to drinking water quality as defined by the World Health Organization "Guidelines for Drinking-water Quality" 4th Edition 2011, or other similar standards. The skilled person will appreciate that additional filtering would be required if this standard was not met e.g. water from a bore hole.

The inlet fitting 42 of the pre-treatment system 40 is fluidly connected to a water source, such as a tap, by a flexible hose. Similarly, the outlet fitting 70 of the pretreatment system 40 is fluidly connected to an inlet of the primary treatment system 80 by a flexible hose. An outlet of the primary treatment system 80 is fluidly connected to an inlet of the dialysis machine 20 by a flexible hose. A drain port of the dialysis machine 20 is fluidly connected to a drain by a flexible hose. The primary treatment system 80 may also have a drain port which may also be fluidly connected to the drain by a flexible hose.

The pre-treatment system 40 functions to soften the incoming water, and to perform an initial particle filtration and chlorine removal. The pre-treatment system 40 features leak detection, pressure regulation, pressure indication, backflow prevention, flow isolation, and sample ports. The 5 μm depth filter 54 filter housing is provided with a differential pressure gauge 56 to detect any blockage of the filter 54.

The primary treatment system 80 functions to remove chemical contaminants and microbiological contaminants. The primary treatment system 80 may feature online quality monitors e.g. conductivity, flow diversion, alarms, and a sample port.

Home Use Trolley

An alternative embodiment of the portable unit 190 will now be described with the aid of FIGS. 5 and 6a through 6e. There are a number of common features between the portable unit 90 described above. Alternative and new features have been given reference numbers in the 200s.

The portable unit 190 is intended for a home use setting. In such a setting dialysis may commonly be carried out by the patient themselves in a seated or lying position. The patient may set up the treatment session in the seated position, in an armchair for example, then remain in the seated position throughout the treatment session. Or alternatively, the patient may set up the treatment session from a seated position on a bed, then when the treatment has started recline themselves to a laying position. Preferably the height of the portable unit 190 is approximately 800 mm.

As such the inventors of the portable unit 190 have made ease of use and ergonomics a key aspect of their invention in order to enable a patient to use the invention from a seated position. Various aspects of the portable unit 190 that provide ease of use and improve quality of life for patients undergoing treatment incorporating the portable unit 190.

Figure 5:
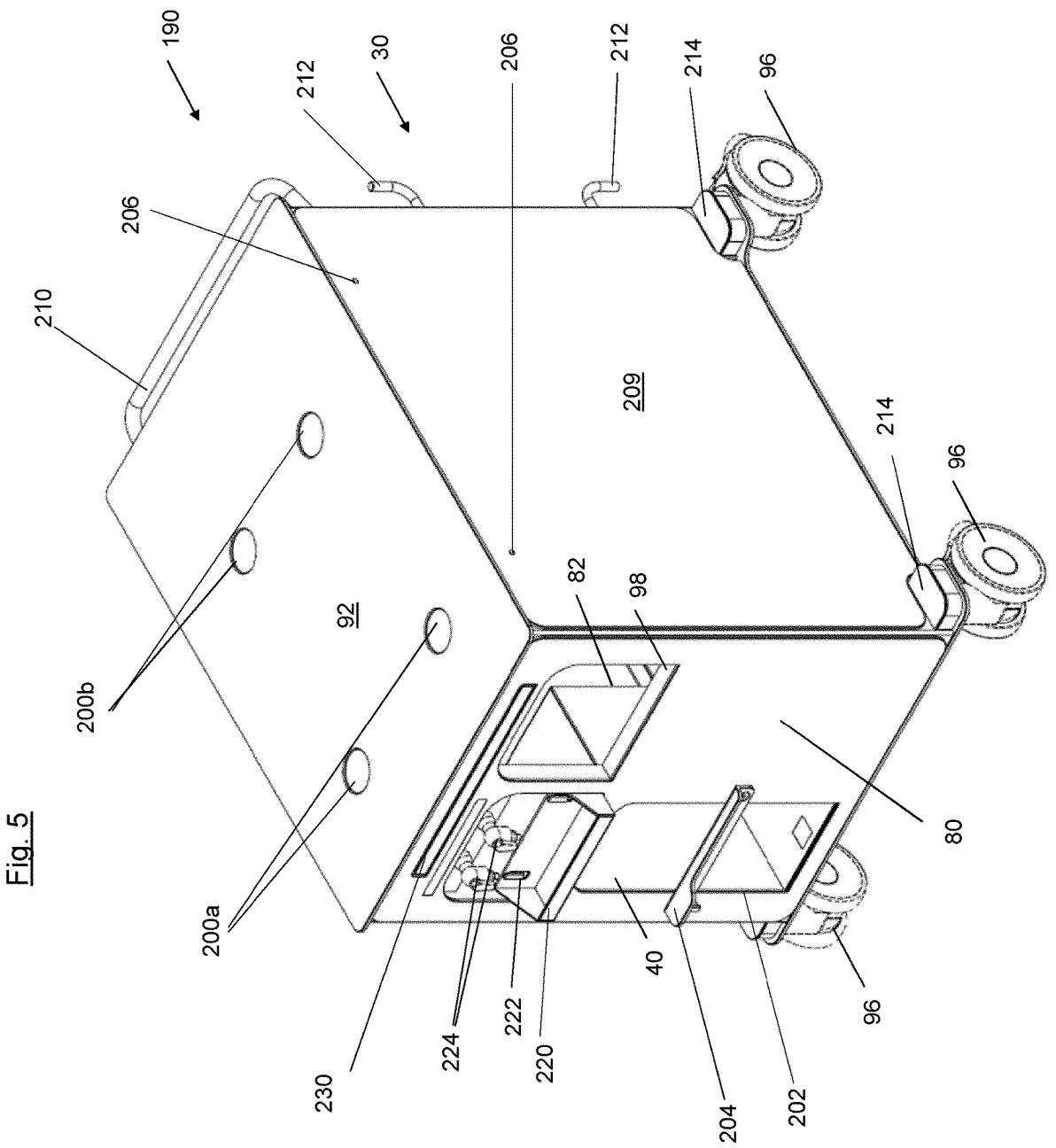
FIG. 5 shows and alternative embodiment of the portable unit.

The portable unit 190 has dialysis machine mounts 200 located on the top surface 92 of the portable unit 190. The dialysis machine mounts 200 are used to both locate and retain the dialysis machine 20 on the top of the portable unit 190. Thus by locating the dialysis machine 20 on the mounts, the dialysis machine 200 is optimally positioned in relation to the portable unit 190. Furthermore the dialysis machine mounts 200 ensure that the dialysis machine 20 engages well with the top surface 92 of the portable unit 190, especially for transit of the portable unit 190. The dialysis machine mounts 200 shown in FIG. 5 are recessed portions of the top surface 92. The recesses 200 are sized to fit feet located on the bottom of the dialysis machine 20 (the coupling is not shown for reasons of clarity). Alternatively other retention means may be used, such as a clip, bolt, screw, ball and detent, collet and rod or other such arrangement.

As shown in FIG. 5, there are four dialysis machine mounts 200a (front mounts 200, back mounts 200b). The two front mounts 200a are located towards the front panel (front view shown in FIG. 6a) the two back mounts 200b are located towards the back panel (back view shown in FIG. 6b). This arrangement having the front mounts 200a towards the front of the portable unit 190 allows the patient to access the dialysis machine 20 control panel 22 from a seated position.

The dialysis machine mounts 200 are arranged to encourage an optimal location of the dialysis machine 20 relative to the portable unit 190. That is, the dialysis machine mounts 200 give a defined orientation for the dialysis machine 20. In the embodiment shown in FIG. 5 this is achieved by the two back mounts 200b. The two back mounts 200b are arranged closer together than the two front mounts 200a which are more spaced apart. The dialysis machine mounts 200, that are complementary to the dialysis feet arrangement, prevents the dialysis machine 20 from being mounted in a non-intended fashion. In alternative embodiments the dialysis machine mount 200 arrangement may be "rotated" by 90, 180, 270 degrees so that the dialysis machine 20 may be mounted in a left side, rear or ride side facing orientation. Due to the recessed nature of the dialysis machine mounts 200, the dialysis machine 20 may still be positioned in an alternate orientation relative to the top surface 92 of the portable unit 190 should the need arise.

The portable unit 190 has two removable panels 208, 209 located on the "left" and "right" sides of the portable unit 190. The removable panels 208, 209 are attached to the portable unit 190 via fasteners 206. The fasteners 206 may be a push latch, or pin which can be pressed by the user to disengage the removable panels 208, 209 from the portable unit 190. Removing the removable panels 208, 209 provides access to the inner space within the portable unit 190 covered by the removable panel 208 or 209.

The removable panels 208, 209 are advantageous as they do not open out into the room to provide access to the inner space of the portable unit 190. If the removable panels 208, 209 were provided as a hinged door then it may be difficult to access the inner spaces in a confined area. The user may simply remove the panel 208, 209 place it to one side, conduct any maintenance required, then re-attach the panel. Such a construction is advantageous in confined spaces such as small rooms or corridors.

Figures 6A, 6B, 6C, 6D, 6E:
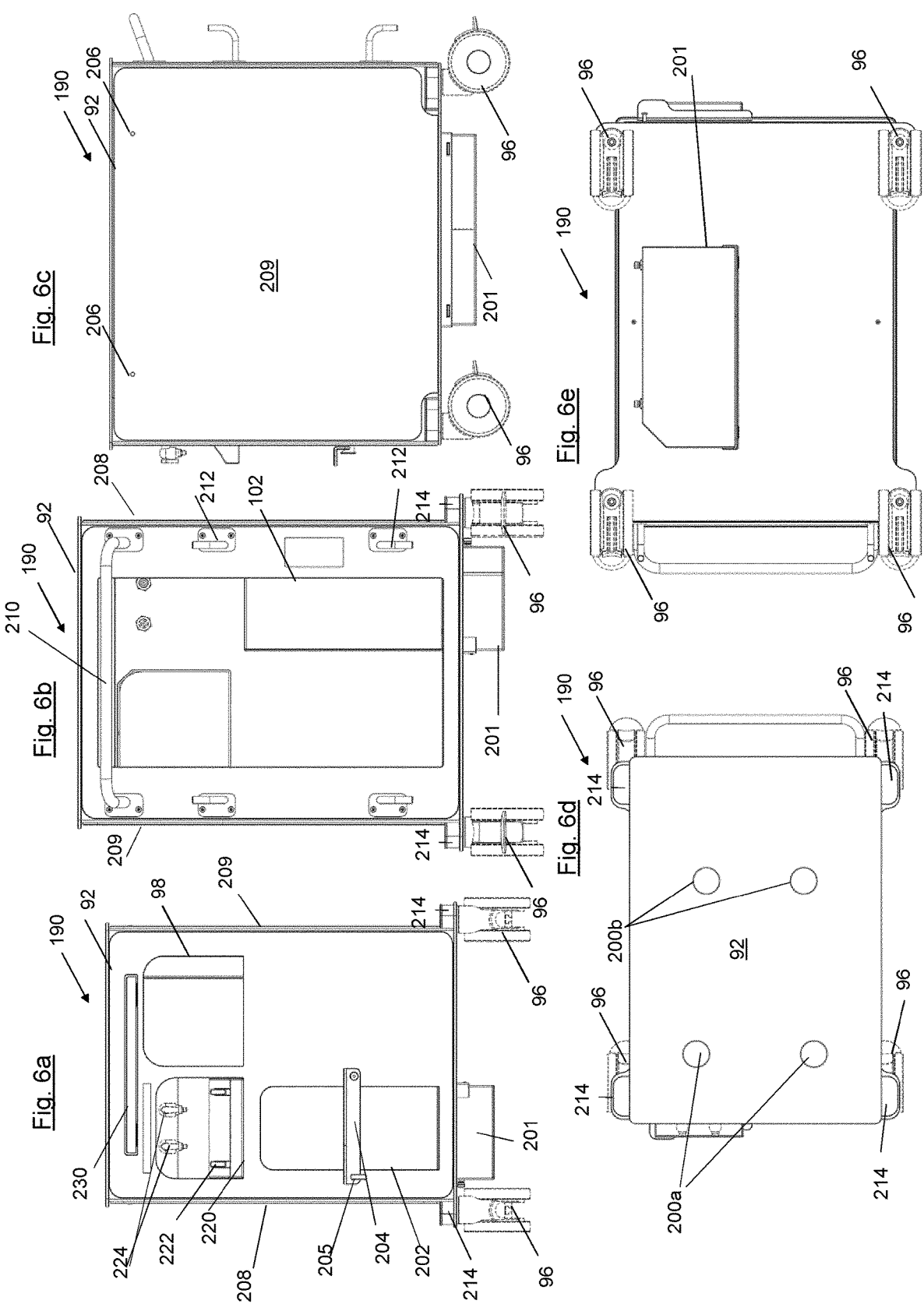
FIGS. 6a to 6e show front, rear, side, upper and lower views of the portable unit of FIG. 5.

The portable unit 190 further comprises a work-surface, deployable shelf 230. The shelf 230 is an extendable and retractable deployable shelf 230. The deployable shelf 230 is located on the front of the portable unit 190 preferably just below the upper surface 92 as shown in FIGS. 5 and 6a. The work-surface provides space for the patient to prepare fluid lines and other consumables prior to beginning a treatment session.

The deployable shelf 230 has at least one push latch arranged operatively with the shelf such that when a user pushes against the front surface of the shelf it actuates the push latch and opens the shelf such that it can be fully deployed.

The shelf 230 may have a retention feature to lock the shelf 230 in the fully extended position until such a time where the user is ready to retract the shelf. The retention feature may be a detent or brake or a latch.

When the user has finished with the shelf 230 they may push it back into the portable unit 190 actuating the push latch allowing the shelf 230 to be fully retained within the portable unit 190. The work-surface can therefore be tidied away when no longer required to save space.

The shelf has a brake to prevent the deployable shelf from extending unintentionally when going up a ramp or over a bump. Alternatively the shelf may have detent which provides the same function.

Alternatively the push latch may have a magnet at the end of a push latch rod that is magnetically connected to a magnet or strip of ferromagnetic material on a surface of the shelf.

In alternative embodiments other latches or catches may be used, for example a magnetic catch, a bales catch, ball and latch, roller catch or a fanlight catch or an alternative latch or locking mechanism.

The portable unit 190 further comprises an acid canister window 202 located on the front face of the portable unit 190 as shown in FIGS. 5 and 6a. The acid canister window 202 is sized to retain an acid canister within it. The acid canister window 202 allows for easy access to the acid canister disposed within, for example for replacement. Further, the acid canister window 202 allows for easy visual inspection of the acid canister, for example to check that the acid canister is correctly connected to the dialysis machine via fluid lines, and that the volume of acid within the acid canister is appropriate.

The fluid lines run from the acid canister around the left hand side of the portable unit 190 and around the front of the portable unit 190. In alternative embodiments at least one or a plurality of clips or fluid line retaining features may be disposed along the side of the portable unit 190 to retain the fluid lines.

The portable unit 190 further comprises a bar 204 and bar retainer 205. The bar 204 is pivotally connected to the front of the portable unit 190 at a pivot point. The pivot point is located next to the acid canister window 202 such that the bar 204 extends across the acid canister window 202. The bar retainer 205 is located on the other side of the acid canister window 202 to the pivot point. The bar 204 pivots from a closed position where it is retained in the bar retainer 205 and an open position where the acid canister window 202 is not covered by the bar 204. The bar 204 is used to retain the acid canister within the acid canister window 202 and prevent the acid canister from falling out. The bar retainer 205 thus prevents further pivoting of the bar 204 and any outward movement of the bar 204, away from the portable unit 190.

The portable unit 190 further comprises at least one tap 224 a removable drip tray 220 and a drip tray mount 222. The removable drip tray 220, tap 224 and drip tray mount 222 are located on the front face of the portable unit 190 above the acid canister window 202. The tap 224 is located above the drip tray 220 and drip tray mount 222. The drip tray 220 is suitable for catching drips from the tap 224 in a volume of the drip tray 220.

The drip tray 220 is mounted removably on the drip tray mount 222. The drip tray mount 222 may be an integral part of the front panel of the portable unit 190.

The ability to remove the drip tray 220 allows the user to clean and removable the drip tray 220 easily.

The portable unit 190 may be provided with one tap 224, two taps 224, or three taps 224, depending upon water sampling requirements.

The portable unit 190 further comprises a handle 210 located on the back side of the portable unit 190. The handle 210 is used to push and/or pull the portable unit 190 when it is being manouvered.

The portable unit 190 further comprises cable/hose tidies 212. The cable/hose tidies 212 are located below the handle 210. The cable/hose tidies 212 are used to tidy fluid lines and/or electrical cables of the portable unit 190 and the dialysis machine 20, when the portable unit 190 is being transported.

The portable unit 190 further comprises a sump 201. The sump 201 is located on the base of the trolley as shown in FIGS. 6a to 6c and 63. The sump 201 is removably connected to the portable unit 190. The sump 201 is attached to the portable unit 190 using two spring loaded screws and a pivot point on the back edge of the sump 201. This arrangement allows easy removal of the sump 201.

Sump 201 is removable for two reasons:

1) to remove water and clean the sump 201; and
2) also it provides a means for access the bottom of the filters 62, 66.

The filters 62, 66 may be provided with access taps/ports on filters 62, 66 so that they can be drained by access to drain for taps via a drain hose. The removal of sump 201 provides access to the bottom of the filters 62, 66.

The sump 201 serves three locations of the portable unit 190. The sump 201 collects water from filters, the RO system and any other point where water may leak or spill.

The sump 201 may be provided with a leak sensor. The leak sensor is arranged in the sump 201 such that the presence of any water (or alternatively a predetermined volume of water) in the sump 201 trips a leak sensor.

Further, in the portable unit 290, the castors 96 are located are provided at a extended corner 214 of a lower surface of the lower panel of the enclosure which extends outwards from the main body of the portable unit. The extended corner 214 widens the base of the portable unit 190 and therefore increases the stability of the portable unit 190. Each of the castors 96 have a lockable brake.

Clinic Use Trolley

An alternative embodiment of the portable unit 290 will now be described with the aid of FIGS. 7 and 8a through 8e. There are a number of common features between the portable unit 190 described above. Alternative and new features have been given new reference numbers in the 300s.

The present portable unit 290 is intended for use in a clinic type setting. For example, in a renal unit, dialysis ward or acute care ward. The portable unit 290 is therefore intended for use by a clinician or medical professional in a standing position with the patient being seated/reclined in a chair or bed or lying in a bed located adjacent to the portable unit 290. The portable unit 290 is taller than the portable unit 190, preferably the height of the portable unit 290 is approximately 970 mm.

The dialysis mounts 300 of portable unit 290 are located further back from the front of the portable unit 290 as compared to portable unit 290.

The portable unit 290 does not have a deployable shelf 230, instead portable unit 290 has a drawer 330 with a drawer handle 332. This is shown in FIGS. 7 and 8a.

Figure 7:
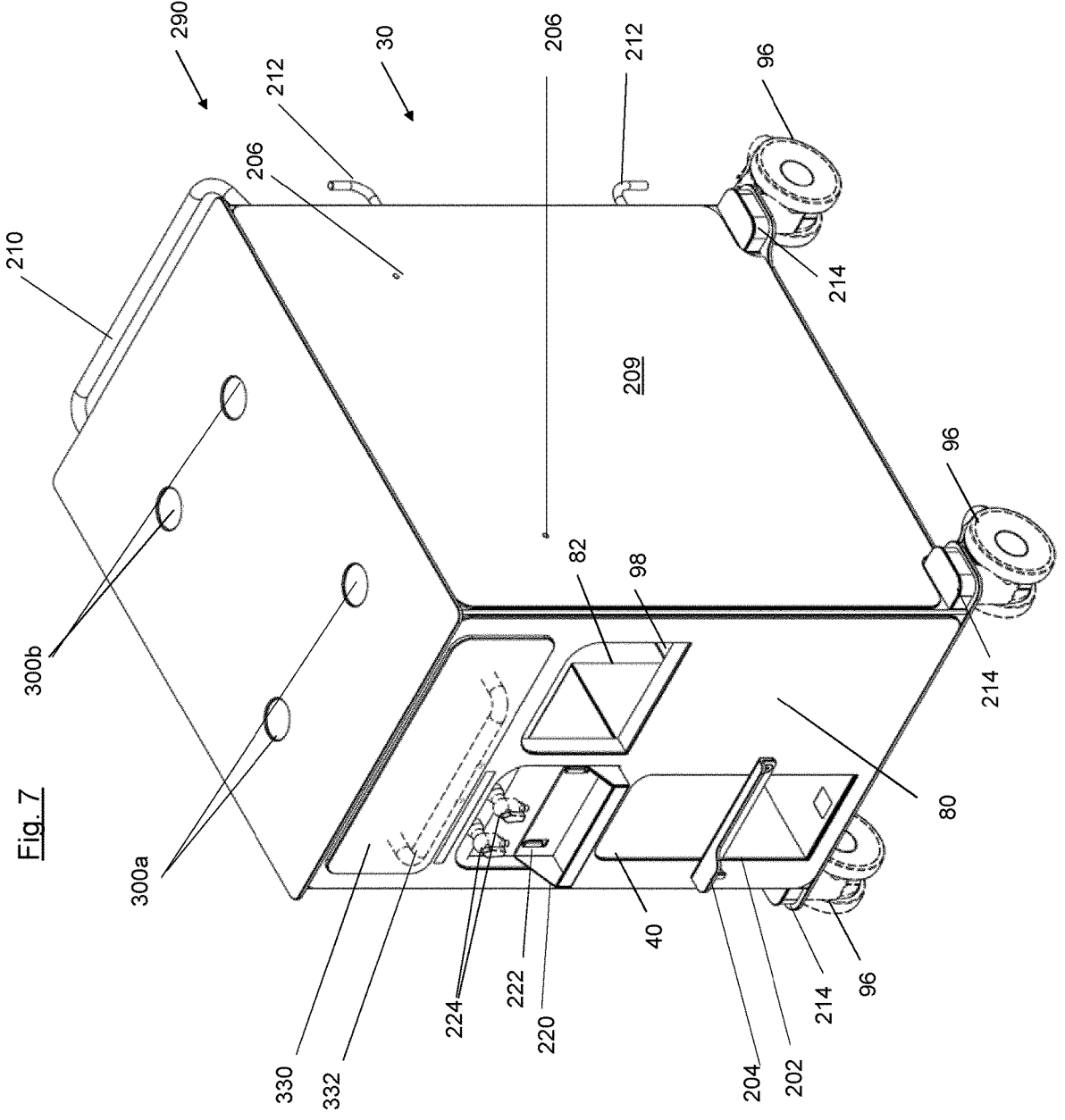
FIG. 7 shows and alternative embodiment of the portable unit.

The drawer 330 is located on the front of the portable unit 290 preferably just below the upper surface 92 as shown in FIGS. 7 and 8a. The drawer 330 may be used to store consumables, spares and/or other bits of equipment in. The drawer 230 also provides space and work-surface for the clinician or medical professional to prepare fluid lines and other consumables prior to beginning a treatment session.

The drawer 330 has at least one push latch arranged operatively with the shelf such that when a user pushes against the front surface of the shelf it actuates the push latch and opens the drawer 330 such that it can be fully deployed by the user pulling on the handle 332.

The drawer 330 may have a retention feature to lock the drawer 330 in the fully extended position until such a time where the user is ready to retract the shelf. The retention feature may be a detent or brake or a latch.

When the user has finished with the drawer 330 they may push it back into the portable unit 290 actuating the push latch allowing the drawer 330 to be fully retained within the portable unit 290. The work-surface can therefore be tidied away when no longer required to save space.

The drawer 330 has a brake to prevent the drawer 330 from extending unintentionally when going up a ramp or over a bump. Alternatively the drawer 330 may have detent which provides the same function. Alternatively the push latch may have a magnet at the end of a push latch rod that is magnetically connected to a magnet or strip of ferromagnetic material on a surface of the drawer 330. In alternative embodiments other latches or catches may be used, for example a magnetic catch, a bales catch, ball and latch, roller catch or a fanlight catch or an alternative latch.

Flat Pack

Any of the portable units 90, 190, 290 may be supplied as a flat pack arrangement. The flat pack containing all of the individual components of the portable unit 90, 190, 290. Optionally, the flat pack may contain tools used to assemble the flat pack.

LIST OF REFERENCE NUMERALS 10 dialysis system
20 dialysis machine
22 dialysis machine control panel
30 water purification system
40 pre-treatment system
42 inlet fitting
44 leak sensor
46 leak detector
48 back flow prevention device
50 pressure reducing valve
54 5 μm depth filter
56 differential pressure gauge
58 external softener bypass
60 bypass isolator tap
62 primary carbon filter
64 chlorine sample port
66 secondary carbon filter
68 second tap
70 outlet fitting

12

80 primary treatment system
82 primary treatment system control panel
90 portable unit
92 upper surface
94 side panel
96 castor
98 window
100 sump
102 rear access window
106 fasteners
190 portable unit
200 dialysis machine mount
200a front mounts
200b back mounts
201 sump
202 acid canister window
204 bar
205 bar retainer
206 fastener
208 removable panel
209 removable panel
210 handle
212 cable/hose tidy
214 extended corner
220 drip tray
222 drip tray mount
224 tap
230 deployable shelf
290 portable unit
300 dialysis machine mount
300a front mounts
300b back mounts
330 drawer
332 drawer handle

The invention claimed is:

1. A dialysis system comprising:
a dialysis machine; and
a water purification system including
    a pre-treatment system, and
    a primary treatment system,
wherein
    the water purification system includes a portable unit defining an enclosure, and
    the dialysis machine is removably provided on an upper surface of the enclosure of the portable unit, and the portable unit is between about 800 and 970 mm in height.

2. The dialysis system of claim 1, wherein the pre-treatment system is arranged on a removable panel of the enclosure.

3. The dialysis system of claim 1, wherein the pre-treatment system comprises a fluid path including a particulate filter, a primary carbon filter and a secondary carbon filter.

4. The dialysis system of claim 1, wherein the primary treatment system comprises a reverse osmosis machine.

5. The dialysis system of claim 4, wherein the reverse osmosis machine has a control panel, and wherein a window is formed in the enclosure aligned with the control panel of the reverse osmosis machine.

6. The dialysis system of claim 1, wherein the primary treatment system comprises a deionisation system.

7. The dialysis system of claim 6, wherein the deionisation system has a control panel, and wherein a window is formed in the enclosure aligned with the control panel of the deionisation system.

8. The dialysis system of claim 1, wherein the water purification system further comprises an endotoxin retentive filter.

9. The dialysis system of claim 1, wherein the water purification system further comprises an ultraviolet light system.

10. The dialysis system of claim 1, wherein the portable unit comprises a trolley.

11. The dialysis system of claim 10, wherein the trolley includes a plurality of castors arranged at least at corners of the enclosure, and/or the trolley includes a plurality of castors including lockable brakes.

12. The dialysis system of claim 1, wherein the enclosure is formed from flat sheet plastic.

\*    \*    \*    \*    \*